(12) United States Patent
Kara et al.

(10) Patent No.: US 11,265,644 B2
(45) Date of Patent: Mar. 1, 2022

(54) HEARING PROTECTION DEVICES, SPEAKERS AND NOISE EXPOSURE SENSORS THEREFORE, AND SENSOR HOUSINGS AND ASSOCIATED METHODS FOR THE SAME

(71) Applicant: HONEYWELL INTERNATIONAL INC., Morris Plains, NJ (US)

(72) Inventors: Peter Kara, Morris Plains, NJ (US); Erik Pertot, Morris Plains, NJ (US); Viggo Henriksen, Morris Plains, NJ (US); Tomas Brhel, Morris Plains, NJ (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 16/881,585

(22) Filed: May 22, 2020

(65) Prior Publication Data
US 2020/0374622 A1 Nov. 26, 2020

(30) Foreign Application Priority Data
May 24, 2019 (EP) .................................... 19176574

(51) Int. Cl.
*H04R 1/10* (2006.01)
*A61F 11/14* (2006.01)
(Continued)

(52) U.S. Cl.
CPC ............ *H04R 1/1083* (2013.01); *A61F 11/14* (2013.01); *H04R 1/1008* (2013.01);
(Continued)

(58) Field of Classification Search
CPC .. H04R 1/1008; H04R 1/1066; H04R 29/001; H04R 1/1083; H04R 1/1041
(Continued)

(56) References Cited

U.S. PATENT DOCUMENTS

| 6,597,792 B1 | 7/2003 | Sapiejewski et al. |
| 8,130,970 B2 * | 3/2012 | Heringslack ............ A61F 11/14 |
| | | 381/71.6 |

(Continued)

FOREIGN PATENT DOCUMENTS

EP 1075164 A3 7/2002

OTHER PUBLICATIONS

Extended European Search Report for EP Application No. 19176574.2 dated Dec. 10, 2019, 7 pages.
(Continued)

*Primary Examiner* — Disler Paul
(74) *Attorney, Agent, or Firm* — Alston & Bird LLP

(57) ABSTRACT

A noise sensor is disposed adjacent a speaker within an ear cup of a hearing protection device. The speaker is disposed within a speaker housing and the noise sensor is disposed within a sensor housing, the sensor housing coupled to the speaker housing such that the noise sensor and speaker remain adjacent one another. The noise sensor includes at least a microphone operably coupled to a printed circuit board. The sensor housing defines an axial bore such that the noise sensor can receive acoustic signals via the axial bore. The sensor housing can be coupled to the speaker housing such that the noise sensor is sealed therebetween and receives acoustic signals via a distal end of the axial bore opposite the speaker. A calibration tool can be disposed to the axial bore via the distal end for airtight calibration of the noise sensor.

20 Claims, 14 Drawing Sheets

(51) Int. Cl.
*H04R 5/033* (2006.01)
*H04R 29/00* (2006.01)

(52) U.S. Cl.
CPC ......... *H04R 1/1066* (2013.01); *H04R 5/0335* (2013.01); *H04R 29/001* (2013.01); *A61F 2011/145* (2013.01)

(58) Field of Classification Search
USPC .................................. 381/71.1, 71.6, 74, 72
See application file for complete search history.

(56) References Cited

U.S. PATENT DOCUMENTS

| | | | | |
|---|---|---|---|---|
| 9,466,281 | B2* | 10/2016 | Hoang Co Thuy | G10K 11/175 |
| 10,102,843 | B1* | 10/2018 | Le | H04R 1/1075 |
| 10,561,532 | B2* | 2/2020 | Bui | H04R 1/1041 |
| 2005/0123146 | A1* | 6/2005 | Voix | H04R 29/00 381/60 |
| 2009/0010474 | A1 | 1/2009 | Ouryouji | |
| 2010/0008529 | A1 | 1/2010 | Oxford | |
| 2016/0314779 | A1 | 10/2016 | Huang | |
| 2017/0245787 | A1* | 8/2017 | Brown | A61B 5/123 |
| 2018/0098143 | A1* | 4/2018 | Silvestri | H04R 1/02 |
| 2018/0255394 | A1* | 9/2018 | Colich | H04R 1/2807 |

OTHER PUBLICATIONS

Annex to the communication dated May 21, 2021 for EP Application No. 19176574.
Communication from the Examining Division dated May 21, 2021 for EP Application No. 19176574.
CA Office Action dated Jul. 29, 2021 for CA Application No. 3081172.

* cited by examiner

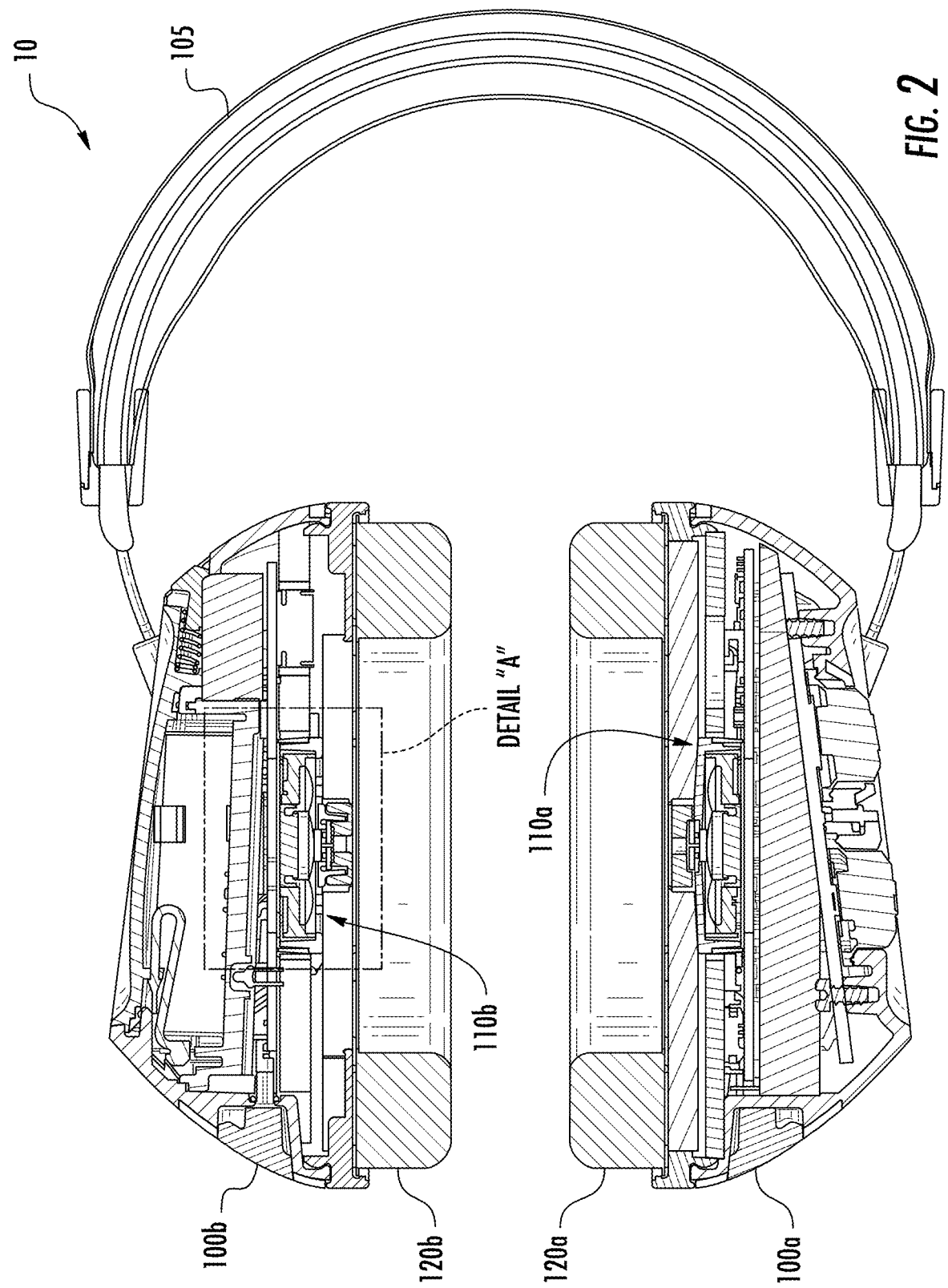

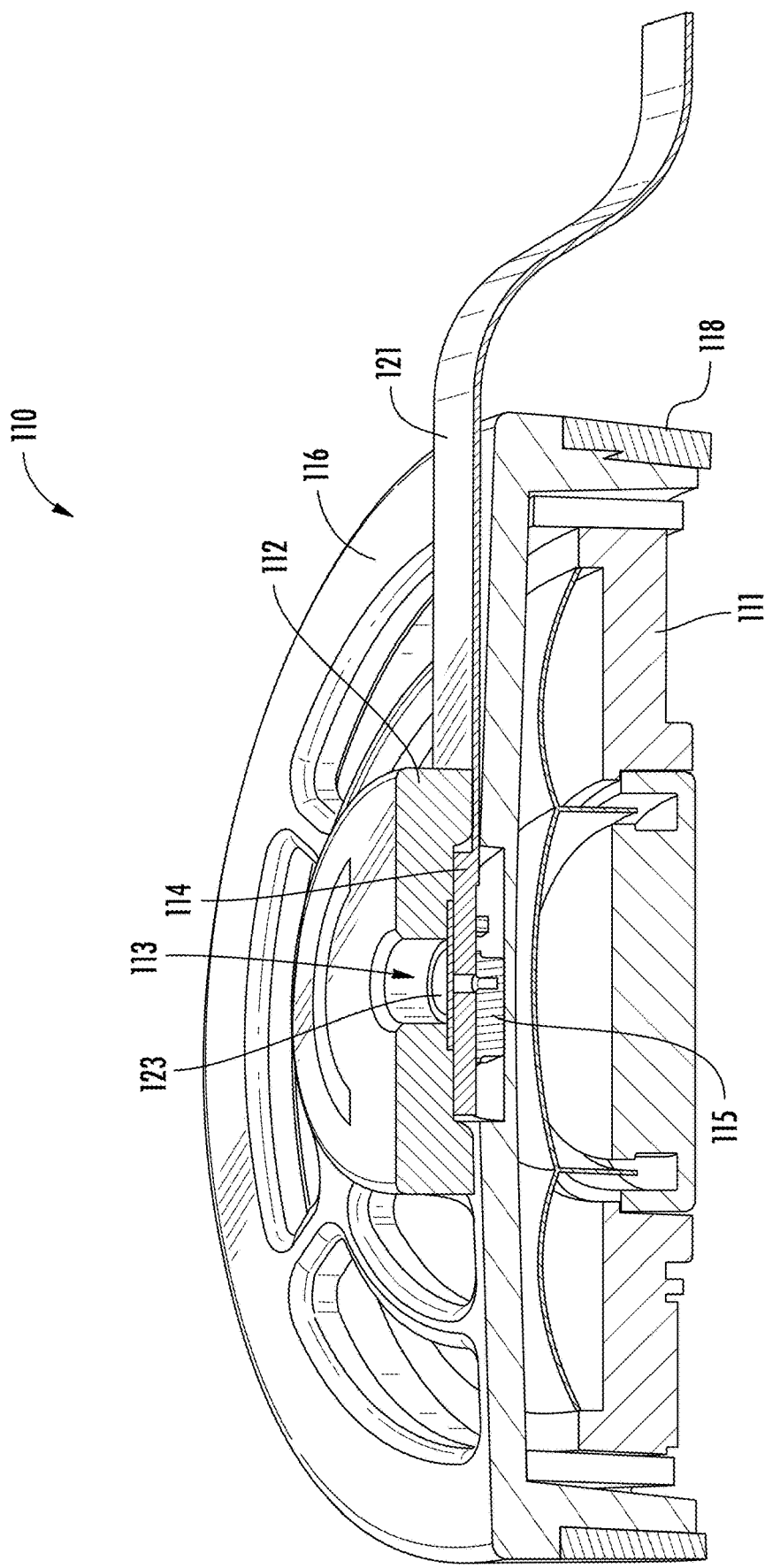

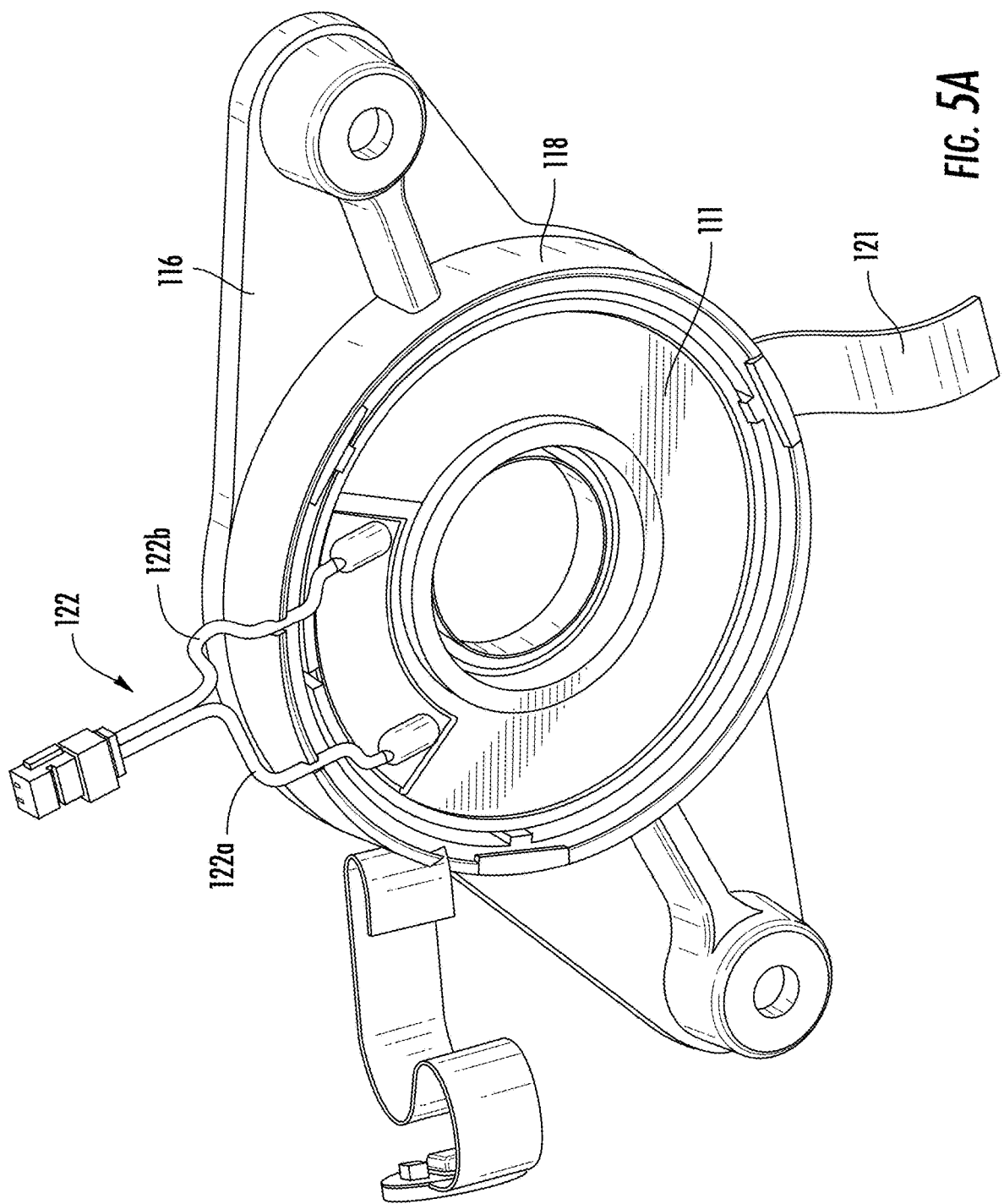

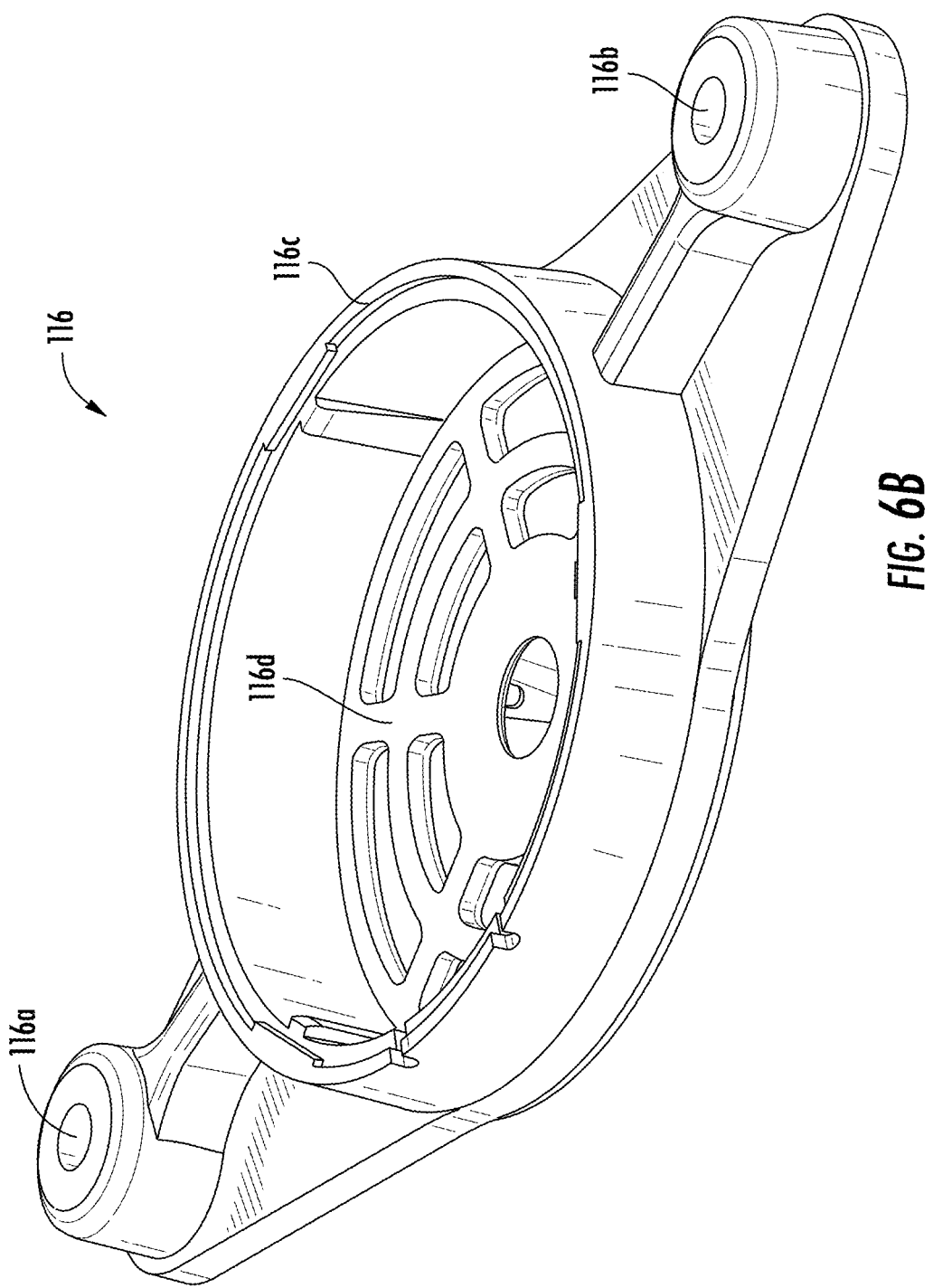

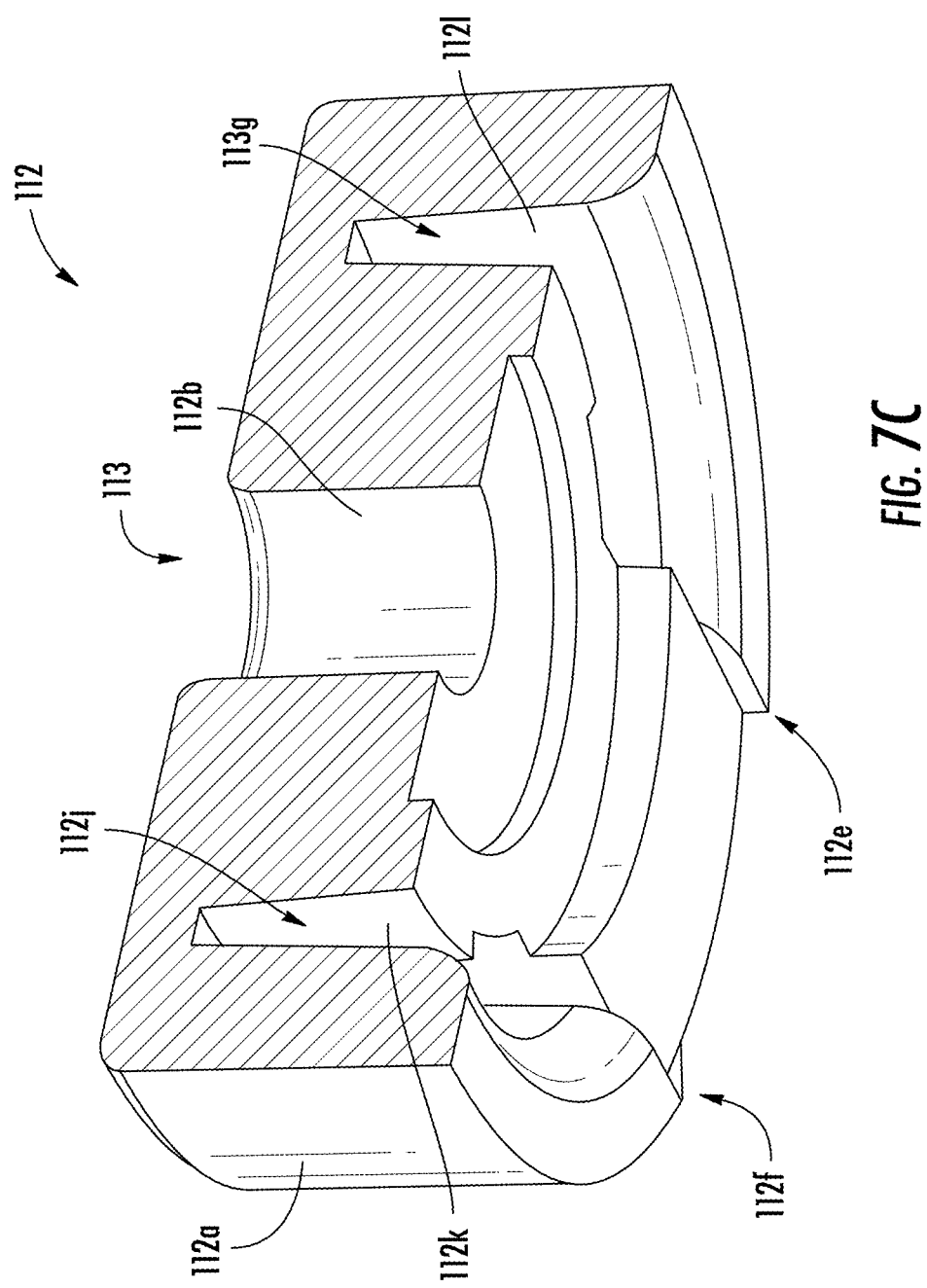

HEARING PROTECTION DEVICES, SPEAKERS AND NOISE EXPOSURE SENSORS THEREFORE, AND SENSOR HOUSINGS AND ASSOCIATED METHODS FOR THE SAME

CROSS-REFERENCE TO RELATED APPLICATIONS

This specification is based upon and claims the benefit of priority from European patent application number EP 19176574.2 filed on May 24, 2019, the entire contents of which are incorporated herein by reference.

BACKGROUND

In the field of hearing protection, hearing protection devices such as earmuffs are often used to protect a wearer's ears from excessive noise exposure. Such hearing protection devices often provide a passive and/or active noise dampening or noise cancellation effect for the wearer, often in an effort to reduce the total noise exposure for a wearer to below a regulated or suggested acute or chronic exposure limit. In such devices, one or more noise sensors can be placed in or about the hearing protection device. However, such noise sensors are often susceptible to damage from exposure to dust and other contaminants, often measure noise exposure in a manner that is not true to the wearer's actual exposure, are costly to manufacture, require significant space within the hearing device, and often cannot be calibrated reliably and/or without substantial disassembly of the hearing protection device. Through applied effort, ingenuity, and innovation, many of these identified problems have been solved by developing solutions that are included in embodiments of the present disclosure, many examples of which are described in detail herein.

SUMMARY

Apparatus, systems, and methods described herein relate to hearing protection devices, speakers and noise exposure sensors therefore, and sensor housings and associated methods for the same. In some embodiments, the hearing protection device can include In some embodiments, the speaker and noise sensor assembly for the hearing protection device can comprise a speaker dimensioned and configured to be disposed within an ear cup of the hearing protection device. In some embodiments, the speaker and noise sensor assembly can further comprise a sensor housing defining an axial bore having a proximal end and a distal end, the sensor housing disposed along a center axis of the speaker. In other words, the sensor housing and the sensor assembly in general can be positioned immediately above and/or abutting the speaker and/or the speaker housing. In some embodiments, the noise sensor can comprise a microphone electrically coupled to the sensor PCB. In some embodiments, the noise sensor can be configured to receive acoustic signals via the axial bore of the sensor housing such that the noise sensor is in acoustic communication with the speaker via the distal end of the axial bore. In some embodiments, the sensor housing can comprise at least one of a vibration attenuation material and a noise dampening material. In some embodiments, the axial bore of the sensor housing comprises a first portion having a first inner diameter and a second portion distal the first portion having a second inner diameter less than the first inner diameter.

In some embodiments, the speaker and noise sensor assembly can be configured such that the sensor housing is engaged with a side of the speaker housing that is opposite the speaker. In some embodiments, the axial bore is open on the distal end and the axial bore is oriented away from the speaker. In some embodiments, the speaker housing can at least partially define a cavity in which the noise sensor is disposed. In some embodiments, the opening at the distal end of the axial bore is only open to the cavity defined at least partially by the speaker housing. In some embodiments, the speaker housing can define a recess configured to receive a portion of the noise sensor therein. In some embodiments, the noise sensor is sealingly disposed against a surface of the sensor housing such that the microphone is positioned at the proximal end of the axial bore. In some embodiments, the axial bore of the sensor housing can be dimensioned and configured to slidably receive a calibration tool to form an airtight seal with an inner surface of the sensor housing, such that the microphone is configured to be disposed within a closed system during calibration.

In some embodiments, the speaker and noise sensor assembly can further comprise a speaker housing disposed proximate the speaker, wherein the sensor housing is engaged with the speaker housing. In some embodiments, the sensor housing can be configured to be securely disposed against a surface of the speaker housing. In some embodiments, the noise sensor can be configured to be disposed in a cavity defined at least partially between the sensor housing and the speaker housing. In some embodiments, the sensor housing can further define one or more securing apertures extending through the sensor housing in a direction substantially parallel to the axial bore. In some embodiments, the one or more securing apertures can be adapted to contact and secure the sensor housing with respect to the speaker housing.

In some embodiments, the speaker and noise sensor assembly can further comprise an internal dust protector disposed between the microphone and the sensor housing, wherein the internal dust protector is disposed between the microphone and the sensor housing to prevent contaminants from contacting the microphone. In some embodiments, the PCB is a microphone PCB and the speaker and noise sensor assembly can further comprise a flexible PCB operably coupled to the microphone PCB. As used herein, sensor PCB and microphone PCB are used interchangeably. In some embodiments, the speaker and noise sensor assembly can further comprise a main PCB operably coupled to the microphone PCB via the flexible PCB.

In some embodiments, the speaker and noise sensor can further comprise a securing member comprising one or more securing ridges, the securing member configured such that the sensor housing can be securely coupled to the securing member by slidably disposing the one or more securing ridges of the securing member into the one or more securing apertures of the sensor housing. For instance, in some embodiments, the securing member can be disposed on or defined by the speaker sensor.

In some embodiments, a hearing protection device can comprise the speaker and noise sensor assembly disposed within an ear cup, the ear cup comprising an external casing, an inside surface, and a cushioning material disposed about the inside surface between the inside surface and the external casing, In some embodiments, the inside surface and/or the cushioning material can define or comprise the ear pad. In some embodiments, in an instance in which the cushioning material is sealably disposed against the user's head about the user's ear, an inner volume of the ear cup is substantially airtight. In some embodiments, the hearing protection device can comprise the speaker and noise sensor assembly as described above, disposed within the ear cup, the hearing protection device further comprising an external noise sensor assembly comprising a second microphone acoustically coupled with an exterior of the hearing protection device, wherein the hearing protection device is configured to compare signals from the noise sensor and the external noise sensor assembly.

As such, in some embodiments, a method of calibrating the noise sensor of the speaker and noise sensor assembly described herein can comprise disposing a calibration tool into the axial bore of the sensor housing via the distal end such that an interior of the calibration tool and the microphone are part of a closed system. In some embodiments, the method can further comprise emitting, by the calibration tool, a calibrating sound having predetermined sound characteristics and receiving, using the microphone, one or more detected sound characteristics of the calibrating sound. In some embodiments, the method can further comprise, in an instance in which a comparison of the one or more detected sound characteristics of the calibrating sound received by the microphone and the sound characteristics of the calibrating sound is indicative of a calibration error, calibrating the noise sensor relative to the calibrating sound. In some embodiments, the method can further comprise disposing the calibration tool into an axial bore of a sensor housing for an external noise sensor assembly such that an interior of the calibration tool and an external microphone are part of the closed system. In some embodiments, the method can further comprise emitting, by the calibration tool, the calibrating sound having the predetermined sound characteristics and receiving, using the external microphone, the one or more detected sound characteristics of the calibrating sound. In some embodiments, the method can further comprise, in an instance in which a comparison of the one or more detected sound characteristics of the calibrating sound received by the external microphone and the sound characteristics of the calibrating sound is indicative of the calibration error, calibrating the external noise sensor relative to the calibrating sound.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings, which are not necessarily drawn to scale.

FIG. 2 shows a cut-away view of the hearing protection device of FIG. 1.

FIG. 3B shows a cut-away view of a speaker and noise sensor assembly for a hearing protection device, according to an embodiment of the present invention.

FIGS. 5A and 5B show perspective views of the speaker and microphone assembly shown in FIG. 4A.

FIGS. 6A and 6B show, respectively, a top view and a perspective view of a speaker holder from the speaker and microphone assembly shown in FIG. 4A.

FIGS. 7A-7C show, respectively, a perspective view, a top view, and a cut-away view of a microphone housing from the speaker and microphone assembly shown in FIG. 4A.

DETAILED DESCRIPTION

Figure 1:
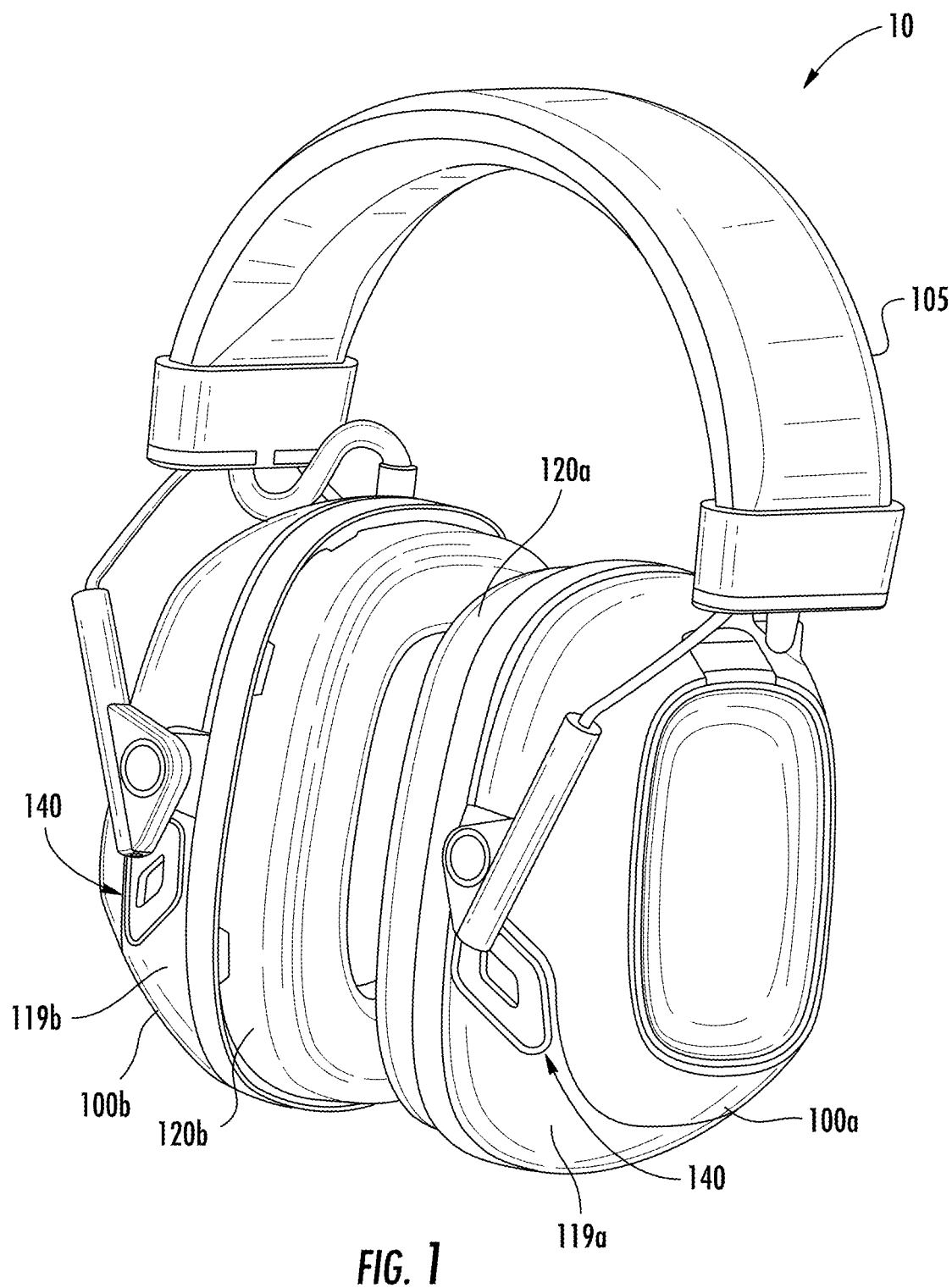
FIG. 1 shows a perspective view of a hearing protection device, according to an embodiment of the present invention.

It should be understood that although illustrative implementations of one or more embodiments are disclosed and discussed below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. The following description of at least one exemplary embodiment is in fact merely illustrative and is in no way intended as a limitation to the present invention and its application or use.

Techniques and devices known to those of ordinary skill in the relevant art may not be discussed in detail but where appropriate, the techniques and devices should be considered as part of the description. Among all the examples shown and discussed herein, any specific value should be construed as merely illustrative and not as a limitation. Thus, other examples of exemplary embodiments may have different values. It should be noted that similar reference numerals and letters denote similar items in the accompanying drawings, and therefore, once an item is defined in a drawing, there is no need for further discussion in the accompanying drawings.

The following brief definition of terms shall apply throughout the application:

The term "comprising" means including but not limited to, and should be interpreted in the manner it is typically used in the patent context;

The phrases "in some embodiments," "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

In the field of hearing protection, hearing protection devices such as earmuffs may be used to protect a wearer's ears from excessive noise exposure. Such hearing protection devices may provide a passive and/or active noise dampening or noise cancellation effect for the wearer, often in an effort to reduce the total noise exposure for a wearer to below a regulated or suggested acute or chronic exposure limit. For instance, an 8 hour maximum daily exposure time may be associated with a noise exposure level of about 85 decibels (dBA), while a person may be limited to 2 hours of exposure time per day for a noise exposure level of 91 dBA, 30 minutes for a noise exposure level of 97 dBA, and seven minutes for a noise exposure level of 103 dBA. By wearing such hearing protection devices, a wearer is able to reduce their noise exposure level, thereby lengthening the maximum daily exposure time such that the wearer can, for example, remain in a higher ambient noise working environment for a longer period of time under such exposure limit regulations. In some embodiments discussed herein, to perform active noise cancellation and/or verify that the hearing protection device is effectively preventing noise exposure during use, one or more noise sensors can be placed in or about the hearing protection device (e.g., on or in an ear cup of a pair of earmuffs). Since these noise sensors must be quite small while also being effective, microelectromechanical system (MEMS) microphones can be used as the noise sensors. Embodiments of the present disclosure facilitate such noise sensors, and may reduce exposure to dust and other contaminants, may measure noise exposure in a manner that is true to the wearer's actual exposure, and may be calibrated reliably and/or without substantial disassembly of the hearing protection device while having a small footprint in the hearing protection device and being cost effective.

Microphones, such as MEMS microphones, for use as a noise exposure sensor in ear muffs or other such hearing protection can often comprise a vibrating diaphragm and a back electrode, forming a capacitor integrated on a silicon wafer, which thereby realizes the acoustic-electric conversion. Such a capacitive microphone may be provided with through holes on its back electrode in order to balance the pressure between the vibrating diaphragm and the back electrode. As the MEMS microphone is exposed to sound waves, the air pressure differential between inside the cavity and outside the cavity changes and air moves through the perforated structure spanning the cavity, the perforated structure (oftentimes a silicone wafer or the like) flexes and sensor detects the change in capacitance between the membrane and the backplate, which affects a voltage variation upon a fixed charge provided to the sensor by an application-specific integrated circuit (ASIC), which corresponds to exposure to a noise having a particular pitch, quality, loudness, amplitude, frequency, etc.

The microphone of such a structure, especially when the cavity about the microphone is sealed and filled with air, has higher acoustic impedance compared to the traditional microphone, and thereby has higher noise attenuation. Since a sealed, air-filled cavity about the microphone can be an important factor in achieving accurate detection of a calibrating noise during in situ calibration, such calibration of the noise sensor microphone and/or a printed circuit board thereof, especially in small and/or complex electronic equipment such as hearing protection devices, may be difficult or impossible for conventional hearing protection devices without significant disassembly of the hearing protection device, or may be completely impossible.

Embodiments of a hearing protection device 10 and associated components disclosed herein are illustrated, by way of example only, in FIGS. 1-8B. In some embodiments, the hearing protection device 10 can include a supporting band 105 connecting a first ear cup 100a to a second ear cup 100b. An ear cup 100a,b can comprise a structural cup 119a,b lined with sound-dampening material 120a,b (also known herein as an "ear pad 120a,b") dimensioned and configured to engage a wearer's head about the wearer's ears such that the sound-dampening material sealably engages the wearer's head. As such, the hearing protection device 10 can be configured to prevent at least some of the ambient noise to which the wearer would otherwise be exposed if not wearing the hearing protection device 10 from reaching the wearer's ears. In some embodiments, each of the ear cups 100a,b of the hearing protection device 10 can further include a speaker and noise sensor assembly 110a,b and, optionally, an exterior noise sensor assembly 140a,b. The first ear cup 100a and the second ear cup 100b can be similar to, a mirror image configurationally of, dissimilar to, or identical to one another. As such, the ear cups 100a,b are hereinafter referred generally as an ear cup 100 and components thereof will be referred to as a speaker and noise sensor assembly 110 and the like, without identifying a particular ear cup.

In some embodiments, the ear pad 120 can be dimensioned and configured to be sealably disposed to a wearer's head about a wearer's ears. In some embodiments, the ear pad 120 can include or be made from a cushioning material, such as a deformable foam or rubber material such that ear pad 120 has a noise dampening effect for the wearer during use of the hearing protection device 10. In some embodiments, in addition to enclosing the wearer's ear within the ear cup 100 and providing comfort, the ear pad 120 can serve a similar purpose as the internal dust protector and/or the external dust protector, which is to at least reduce and possibly prevent the communication of dust and other contaminants into the ear cup 100. In some embodiments, therefore, an interior space defined within the ear cup 100 by at least the ear pad 120, an external casing of the ear cup, and other suitable components (e.g., an external noise sensor) can be airtight or substantially airtight during use by the wearer.

In some embodiments, the speaker and noise sensor assembly 110 can be disposed, positioned, secured about, coupled to, or fixed within the ear cup 100. For instance, in some embodiments, it may be advantageous to position the speaker and noise sensor assembly 110 nearby a speaker 111, in order to reduce the overall profile of the ear cup 100 based on a change in configuration, position, size, and/or form factor of components of the ear cup 100. In some embodiments, the speaker 111 can be positioned approximately in the center of the ear cup 100 and/or nearby the center of the ear pad 120 such that sound emitted by the speaker 111 can be easily heard by a user of the hearing protection device 10. In some embodiments, the speaker and noise sensor assembly 110 can comprise a microphone 115. In some embodiments, the speaker and noise sensor assembly 110 can be configured such that the microphone 115 is positioned adjacent the speaker 111, such as between the speaker 111 and the user's ear when worn by the wearer. In some embodiments, the speaker and noise sensor assembly 110 can be positioned such that noise emitted by the speaker 111 and/or noise that reaches the speaker and noise sensor assembly 110 from outside the ear cup 100, such as from nearby the wearer's ear, external to the ear cup 100 can be measured using the speaker and noise sensor assembly 110. This noise exposure signal can then be used in active noise cancellation to generate a destructively interfering audio signal that is generated via a processor and memory in one or both ear cups 100 (e.g., on a main PCB of the ear cups) and output via the speakers 111 shown in each ear cup. The noise exposure signal may additionally or alternatively be used to compare with a noise exposure signal from a microphone positioned at or proximate the external casing 119 of the ear cup 100 to determine the drop in noise exposure between the exterior and interior of the ear cup 100. In some embodiments, the speaker and noise sensor assembly 110 can be positioned as close to the wearer's ear as possible, such as at or proximate an inner portion of the ear pad 120 of the ear cup 100 near the sound-dampening material. Without wishing to be bound by any particular theory, placing the speaker and noise sensor assembly 110 on or in the ear cup 100 at a position sufficiently nearby the wearer's ear may increase the accuracy of the noise level measured by the microphone 115 relative to actual noise the wearer is exposed to (e.g., from the speaker 111 and/or ambient noise originating outside the ear cup 100) while wearing the hearing protection device 10.

In some embodiments, the speaker and noise sensor assembly 110 can include a sensor housing 112 defining an axial bore 113 therethrough. In some embodiments, the sensor housing 112, a portion of the housing, and/or a portion of the axial bore 113 of the sensor housing 112 can be configured to receive a microphone PCB 114 and/or a microphone 115. In some embodiments, the axial bore 113 of the sensor housing 112 can be configured to transmit noise from inside the ear cup 100 to the microphone 115 or other such sensor disposed and retained within the sensor housing 112. In some embodiments, the microphone 115 or other such sensor disposed within the sensor housing 112 can be disposed on the microphone PCB 114 and may be connected to one or more flexible PCBs 121. In some embodiments, the one or more flexible PCBs 121 can be operably coupled to one or more main PCBs (not shown).

In some embodiments, the microphone 115, which can be any suitable type of microphone such as a microelectromechanical systems—(MEMS)—based microphone or the like, can be mounted on, fixed to, electrically coupled to, soldered to, and/or otherwise coupled to the sensor PCB 114a. In some embodiments, the sensor PCB 114 can be particularly dimensioned and configured such that a portion of the sensor PCB 114 can be retained, with the microphone 115, within the first portion of the axial bore 113 of the sensor housing 112. In some embodiments, the sensor PCB 114 can have any suitable form factor such that the sensor PCB 114 can sealably abut a surface of the axial bore 113 the sensor housing 112. For instance, the sensor PCB 114 can have a form factor that is substantially flat, planar, smooth, round, square, rectangular, quadrilateral, quadrangular, tubular, ellipsoidal, homogenous, even, symmetrical, asymmetrical, or the like. In some embodiments, the sensor PCB 114 or a portion thereof can be at least partially flexible. In some embodiments, the ear cup 100 can further comprise a main PCB (not shown) electrically connected via a flexible PCB 121 to the sensor PCB 114, the sensor PCB 114 configured to be electrically coupled to the microphone 115. In some embodiments, the electrical components mounted to the sensor PCB 114 may be offset from the edges such that the housing 112 can grip the sensor PCB 114. In some embodiments, the main PCB may comprise a processor and memory for performing the signal processing of at least a portion of the hearing protection device, such as the examples described herein. In some embodiments, the sensor PCB 114 can define one or more acoustic apertures 124 through the sensor PCB 114 at a location corresponding to at least a portion of the axial bore 113 of the sensor housing 112. In some embodiments, the microphone 115 can e disposed on a side of the sensor PCB 114 facing the speaker 111 such that the one or more acoustic apertures 124 are open to only one end of the axial bore 113. In some embodiments, the one or more acoustic apertures 124 through the sensor PCB 114 can be substantially aligned with the axial bore 113 in the distal direction such that the one or more acoustic apertures, and as such the microphone 115, are in acoustic communication with the inner volume of the ear cup 100 and the speaker 111 via the distal end (end opposite the speaker 111) of the axial bore 113.

Figure 6A:
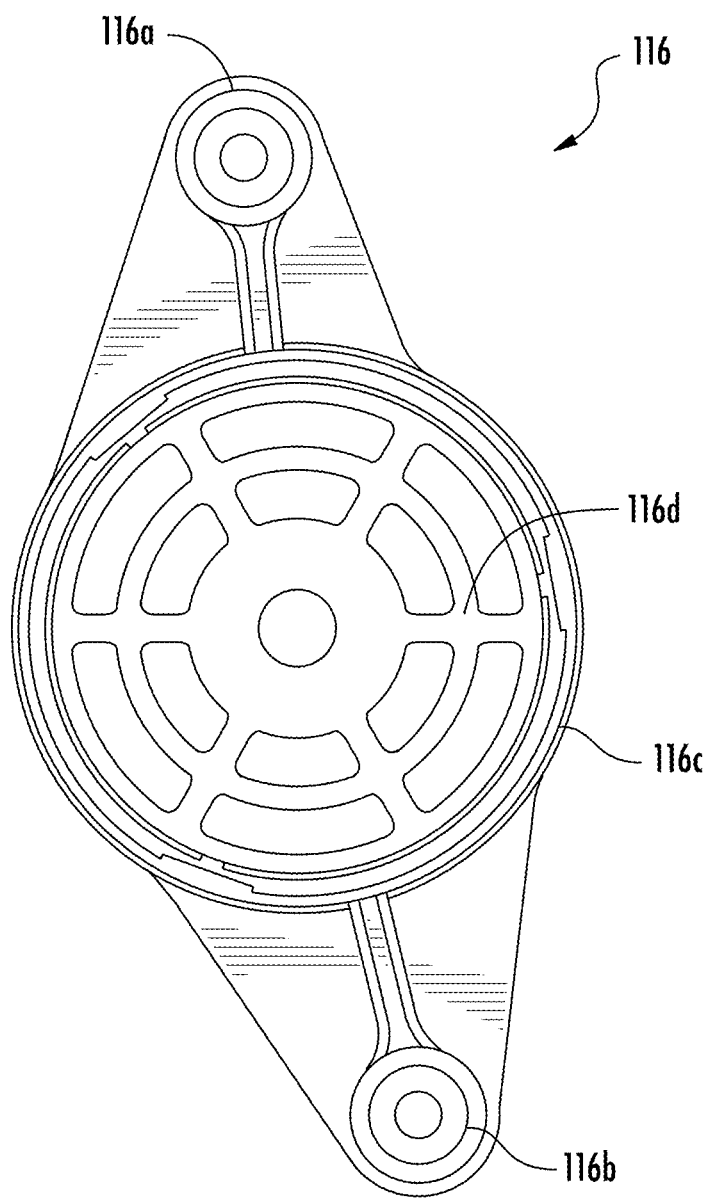
Figure 7A:
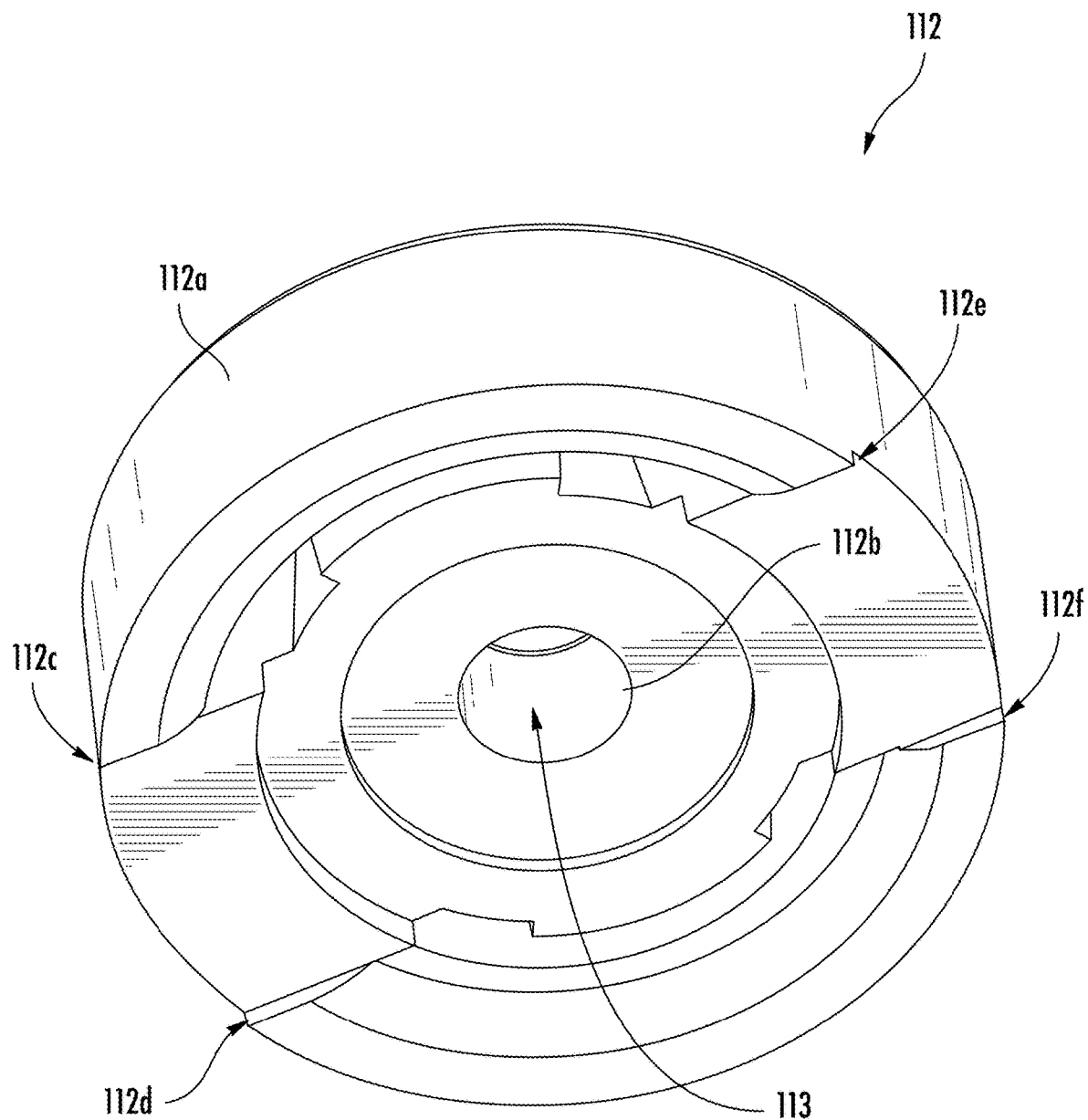
Figure 7B:
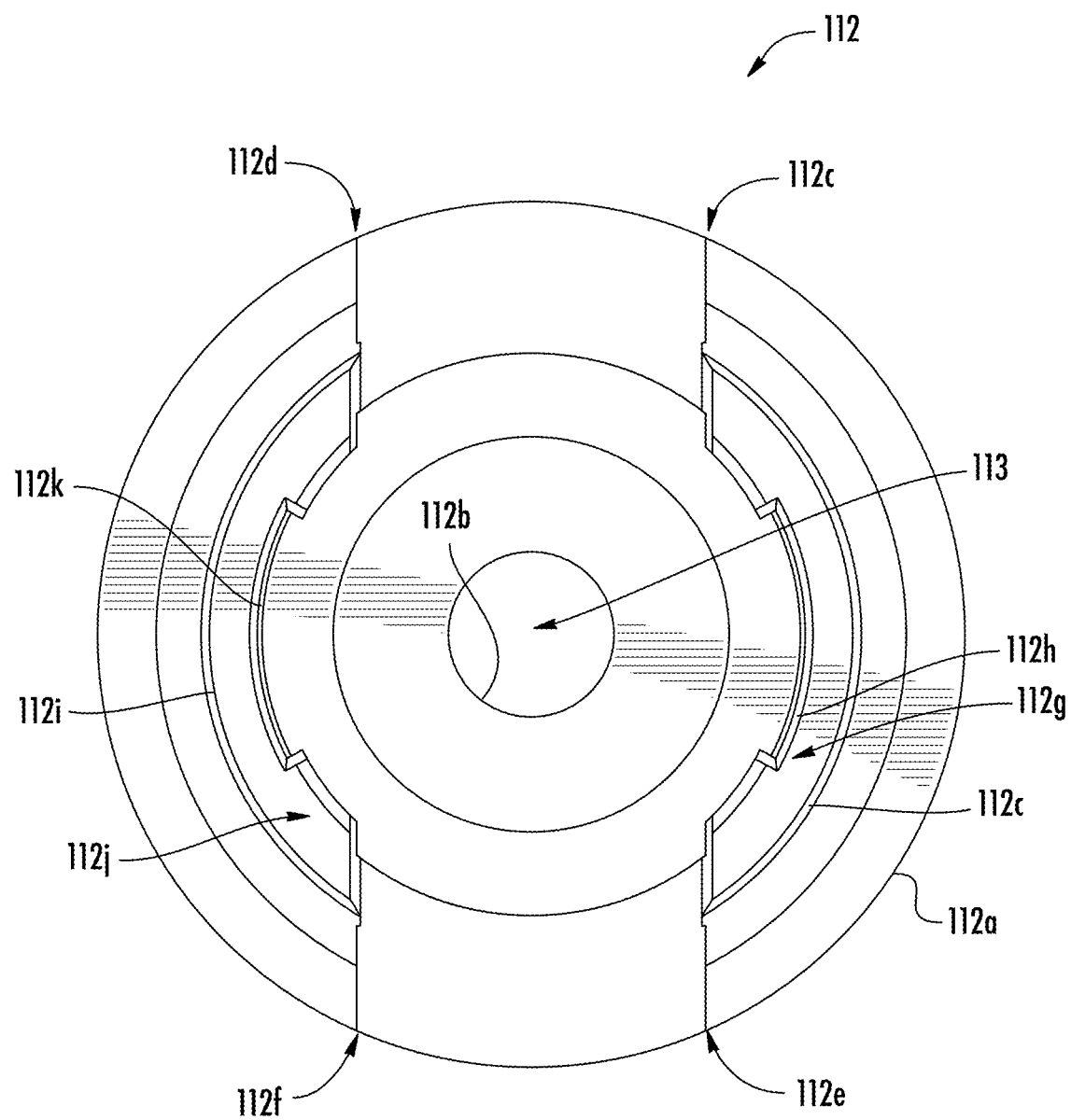
Figure 8A:
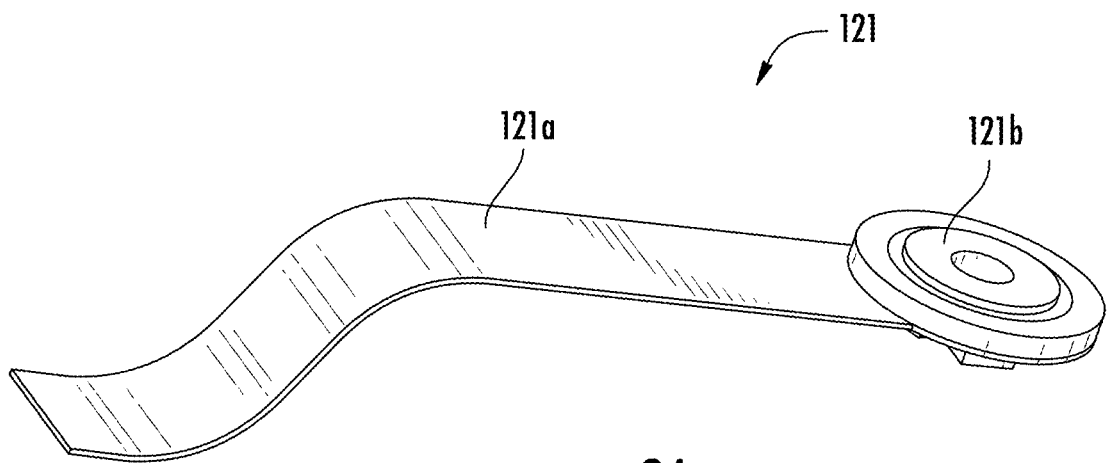
FIGS. 8A and 8B show perspective views of a noise sensor assembly from the speaker and microphone assembly shown in FIG. 4A.
Figure 8B:
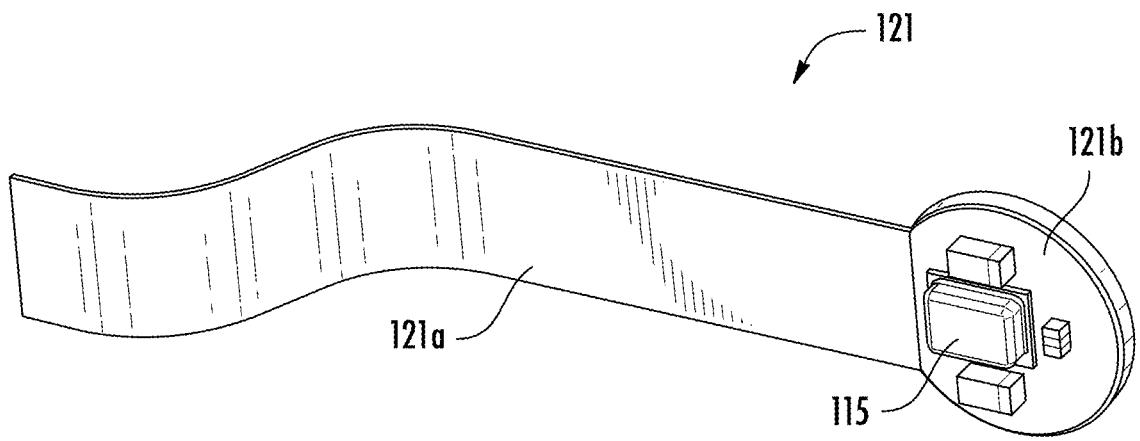

In some embodiments, the speaker 111 can be held in place within the ear cup 100 by a speaker holder 116 and a securing ring 118. In some embodiments, the speaker holder 116 can comprise or define a first fastening portion 116a and a second fastening portion 116b, together the fastening portions, which are configured to secure the speaker holder 116 in place within the ear cup 100. In some embodiments, the speaker holder 116 can further comprise or define a speaker retention portion 116c, such as illustrated in FIGS. 6A and 6B, that has a form factor such that a concavity is formed that dimensionally relates to the speaker 111. In some embodiments, the speaker retention portion 116c can be configured such that the speaker 111 can be retained within the speaker holder 116 by slidably disposing the speaker 111 within the speaker retention portion 116c. In some embodiments, the speaker holder 116 can further comprise a sound communication portion 116d configured to facilitation retention of the speaker 111 within the speaker retention portion 116c while allowing acoustic communication from the speaker 111 therethrough. The sound communication portion 116d can comprise a substantially round, flat portion having one or more holes through the sound communication portion 116d such that sound from the speaker 111 can be communicated through the sound communication portion 116d.

Figure 3A:
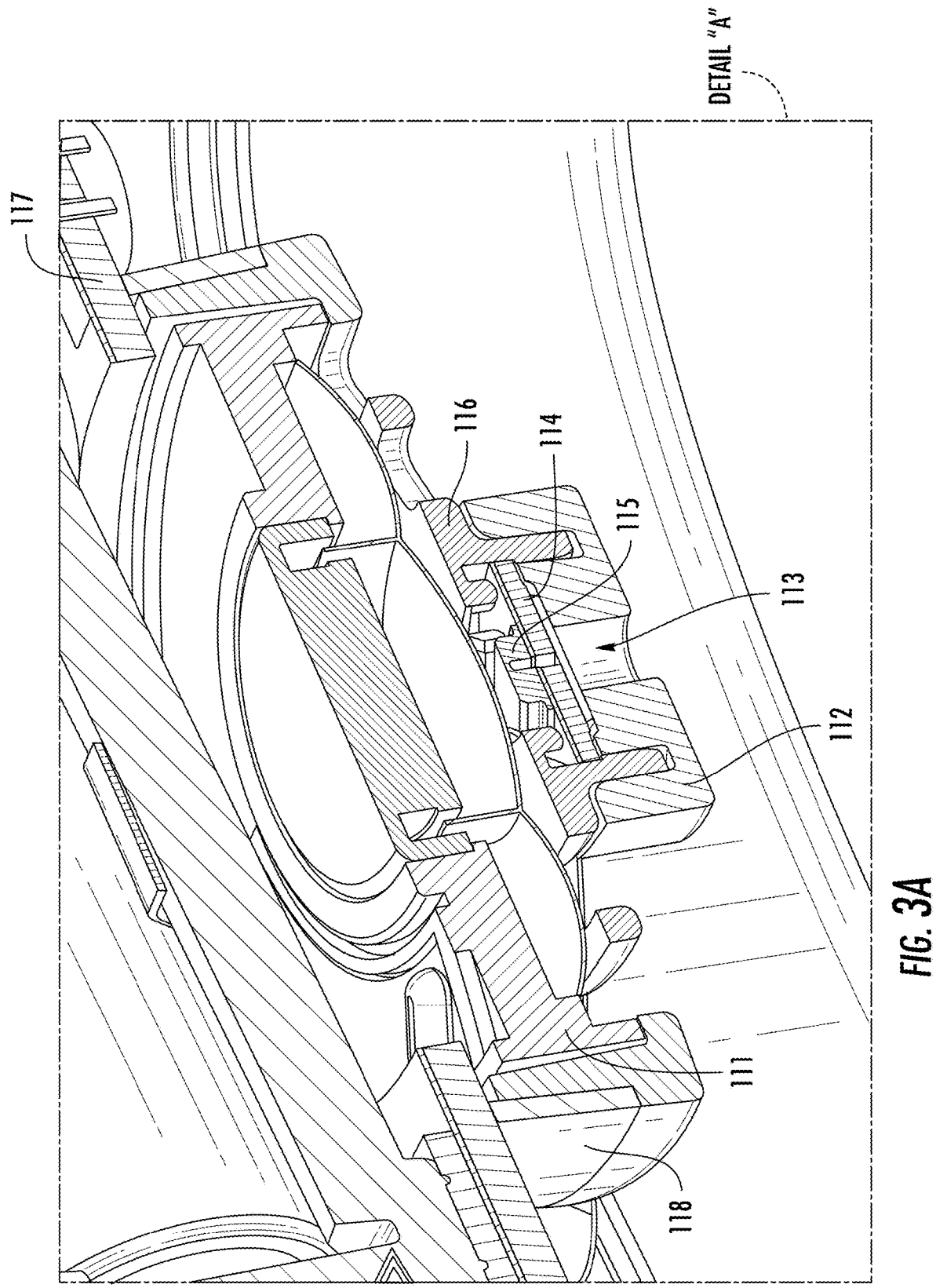
FIG. 3A shows a portion of the cut-away view in FIG. 2 of the hearing protection device of FIG. 1.

In some embodiments, such as illustrated in FIG. 3A, the speaker holder 116 can define a cavity and a center hole through the sound communication portion 116d, the center hole configured such that the microphone 115 can be disposed in or proximate the center hole. In some embodiments, the sensor holder 112 forms some or all of the cavity. In some embodiments, the microphone 115 can be coupled to the sensor PCB 114 to form a sensor assembly. In some embodiments, the sensor assembly can be disposed within the sensor housing 112, the sensor housing 112 disposed to or coupled to the sound communication portion 116d of the speaker housing 116 such that the sensor assembly, comprising the microphone 115 and the sensor PCB 114, is disposed in or proximate the center hole of the sound communication portion 116d of the speaker housing 116.

In some embodiments, such as illustrated in FIG. 3B, the speaker holder 116 can define a cavity in or proximate the center of the sound communication portion 116d. In some embodiments, the cavity is configured such that the microphone 115 can be disposed in or proximate the cavity. In some embodiments, the sensor holder 112 forms some or all of the cavity. In some embodiments, the microphone 115 can be coupled to the sensor PCB 114 to form the sensor assembly. In some embodiments, the sensor assembly can be disposed within the sensor housing 112, the sensor housing 112 disposed to or coupled to the sound communication portion 116*d* of the speaker housing 116 such that the sensor assembly, comprising the microphone 115 and the sensor PCB 114, is disposed in or proximate the cavity of the sound communication portion 116*d* of the speaker housing 116. As such, in some embodiments, the sensor assembly can be sealed in a substantially airtight space defined by the cavity of the speaker holder 116, the microphone 115, the sensor PCB 114, and/or the sensor housing 112, which space may, in some embodiments, only be open via the distal end of the axial bore when a calibration tool is not inserted.

In some embodiments, the sound communication portion 116*d* of the speaker housing 116 can be dimensioned and configured such that the sensor housing 112 can be fixably coupled to the sound communication portion 116*d* of the speaker housing 116. In some embodiments, the sensor housing 112 can define one or more openings 112*j*, 112*e* extending through some or all of the sensor housing 116 in a direction substantially parallel with the axial bore 113. In some embodiments, the speaker housing 116 can comprise one or more solid features 116*e*, 116*f* that stand proud of the sound communication portion 116*d* of the speaker housing 116. In some embodiments, the one or more solid features 116*e*, 116*f* can be dimensioned and configured such that when the one or more solid features 116*e*, 116*f* are slidably disposed within the one or more openings 112*j*, 112*e*, the sensor housing 112 is securely coupled to the speaker housing 116.

In some embodiments, the sensor housing 112 can be generally columnar in shape, and/or can have any other form factor suitable to facilitate retention of the sensor assembly nearby the speaker and to facilitate the forming of airtight conditions about the sensor assembly 110 during calibration of the noise sensor without significant disassembly of the ear cup 100. In some embodiments, the sensor housing 112 can comprise a generally cylindrical out surface 112*a* and a generally cylindrical inner surface 112*b*. In some embodiments, the generally cylindrical inner surface 112*b* can at least partially define the axial bore 113. In some embodiments, the axial bore 113 can extend through the full length of the sensor housing 112 in an axial direction. In some embodiments, the axial bore 113 of the sensor housing 112 can comprise a first portion having a first inner diameter and a second portion having a second inner diameter less than the first inner diameter. In some embodiments, the first portion of the axial bore 113 can be dimensioned and configured to at least partially retain the sensor assembly, the sensor assembly comprising the microphone 115 and the sensor PCB 114. In some embodiments, the first portion of the axial bore 113 of the sensor housing 112 can comprise a plurality of cut-outs 112*c*-112*f* suitable for allowing the flexible PCB 121 connected to the sensor PCB 114 to extend from inside the first portion of the axial bore 113 to outside of the sensor housing 112. In some embodiments, the sensor housing 112 can further comprise a first opening 112*g* defined at least in part by a first opening surface 112*h* and a second opening surface 112*i*. In some embodiments, the sensor housing 112 can further comprise a second opening 112*j* defined at least in part by a third opening surface k and a fourth opening surface $\ell$.

In some embodiments, the sensor assembly can be configured such that the microphone 115 is in acoustic communication with the inner volume of the ear cup 100 via the axial bore 113 of the sensor housing 112. For instance, in some embodiments, the second portion of the axial bore 113 having the second inner diameter less than the first inner diameter of the first portion of the axial bore 113 can be configured to facilitate acoustic communication between the inner volume of the ear cup 100 and the sensor assembly 110 (e.g., the microphone 115). In some embodiments, the sensor assembly can be configured such that sound can travel through the axial bore 113 of the sensor housing 112, through an aperture in the sensor PCB 114, and to the microphone 113. In some embodiments, a dust protector 123 can be disposed between the sensor assembly and the sensor housing 112, such as between the sensor PCB 114 and the sensor housing 112. In some embodiments, the dust protector 123 can be configured such that sound can be acoustically communicated through the dust protector 123 and to the sensor assembly while preventing ingress of contaminants, such as dust and the like, to the sensor assembly via the axial bore 113 of the sensor housing 112.

Figure 4A:
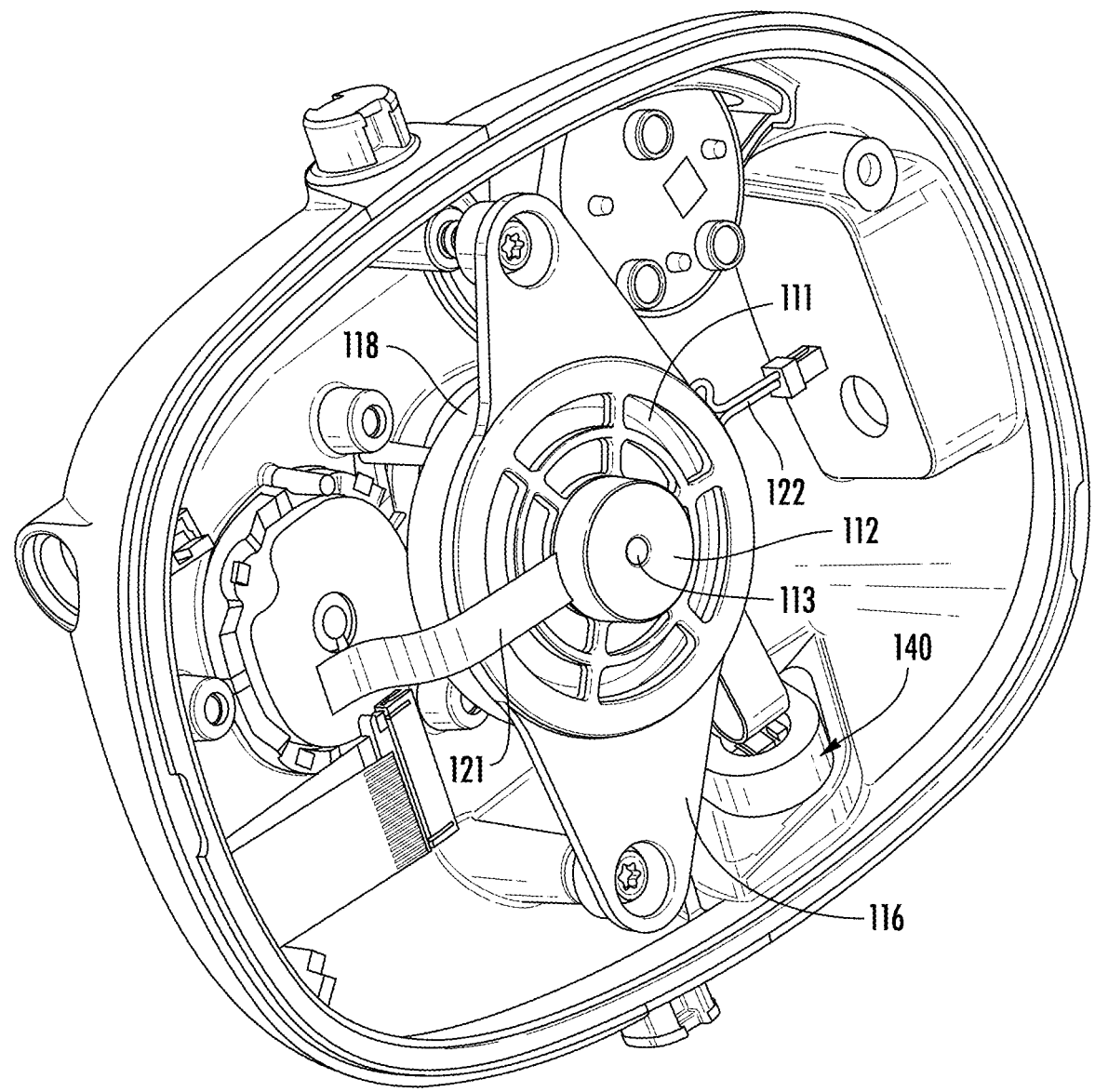
FIG. 4A shows a partially disassembled view of a speaker and microphone assembly in an ear cup of the hearing protection device of FIG. 1.
Figure 4B:
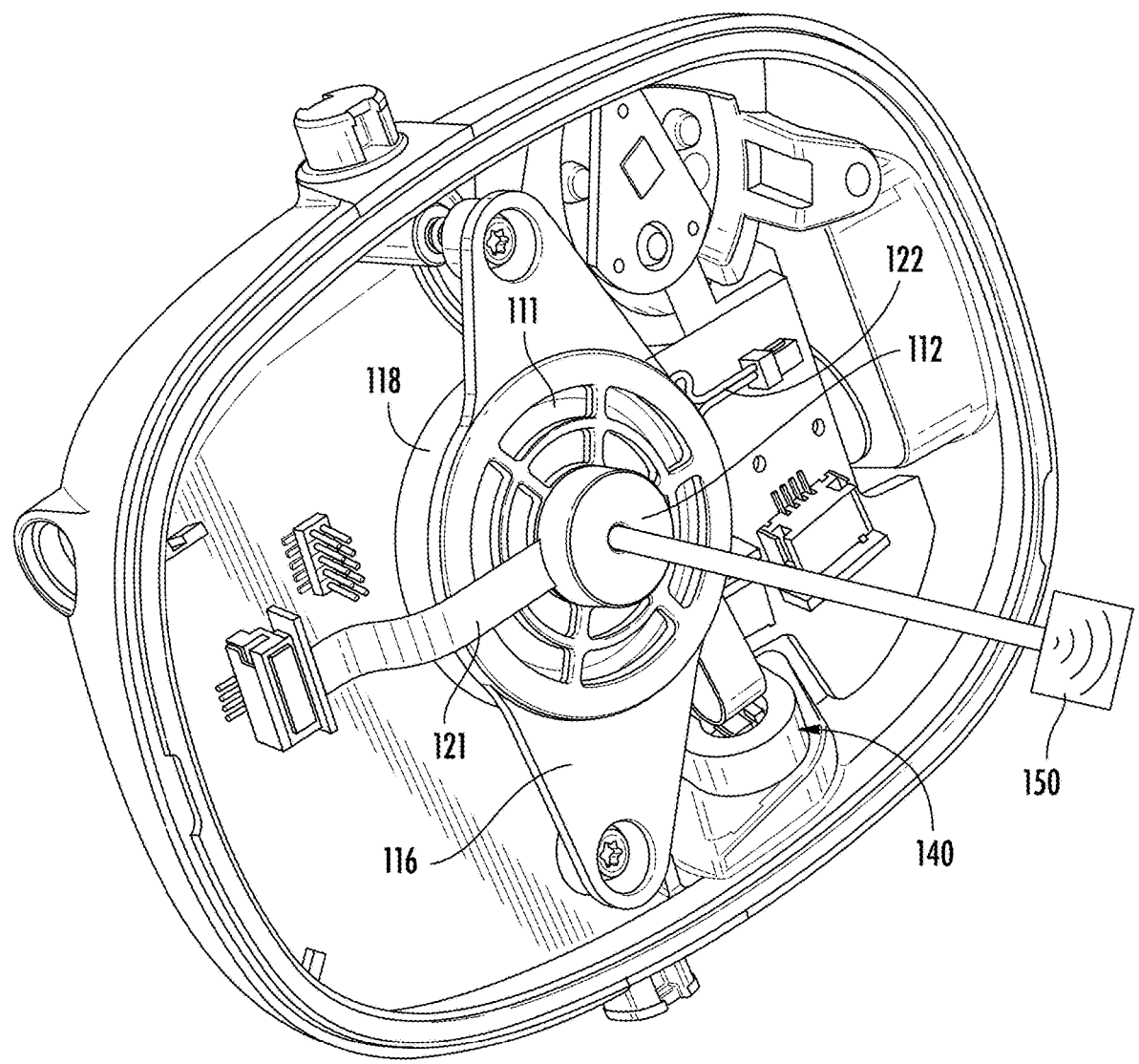
FIG. 4B illustrates an approach for calibrating the speaker and microphone assembly shown in FIG. 4A.
Figure 5B:
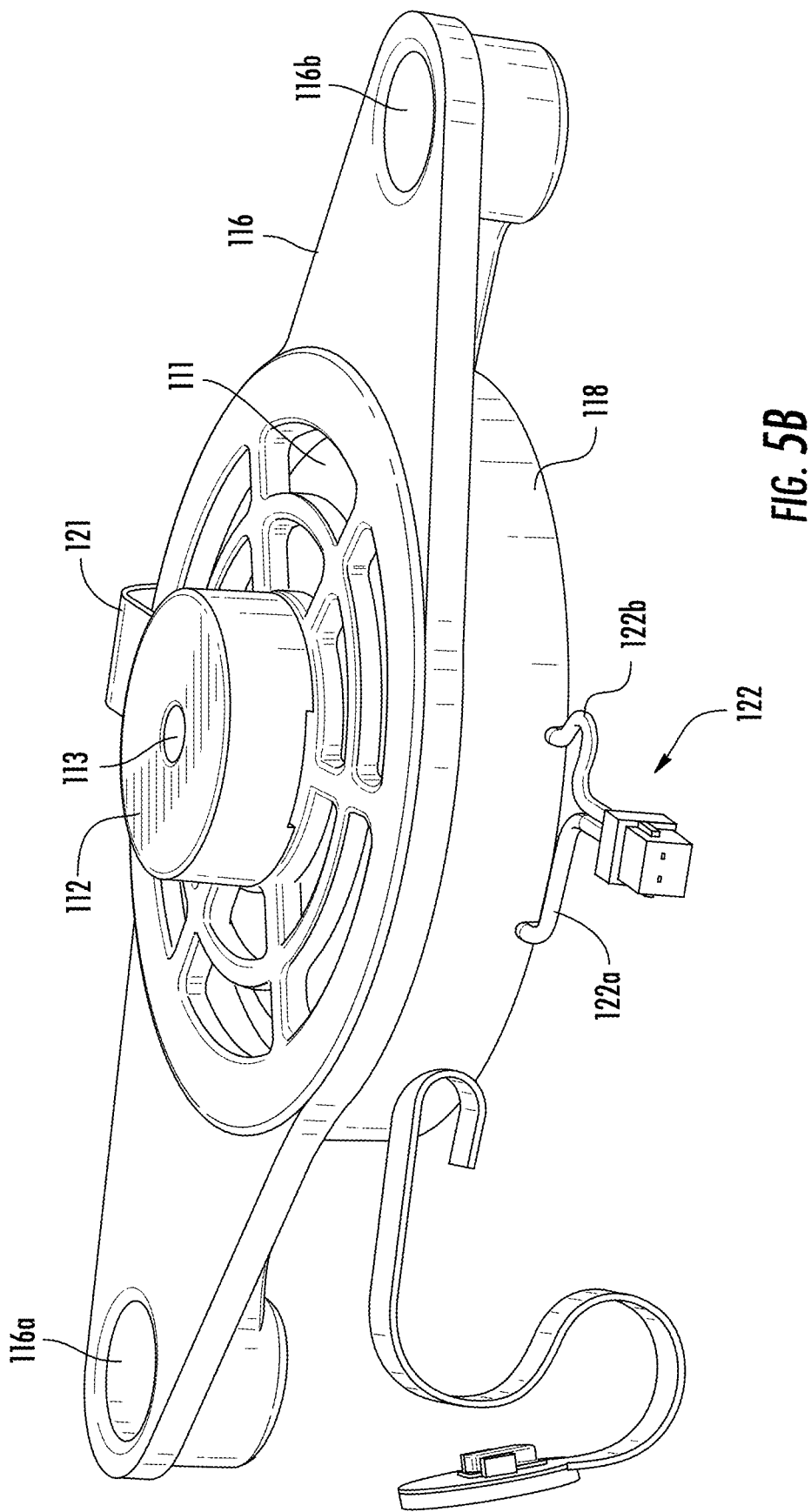

In some embodiments, the speaker and sensor assembly 110 can further comprise speaker electronics 122, such as electrical wiring 112*a,b* configured to communicate a signal to the speaker 111. In some embodiments, the speaker and sensor assembly 110 can be disposed within the ear cup 100 at any suitable location, such as nearby the ear pad 120. In some embodiments, the ear pad 120 or another component of the ear cup 100 can be removed such that a calibration tool 150 can be used to calibrate the sensor assembly, such as illustrated in FIG. 4B. For instance, in some embodiments, the method of calibrating the sensor assembly (e.g., the microphone 115 and/or the sensor PCB 114) can comprise at least slidably disposing the calibration tool 150 into the axial bore 113 of the sensor housing 112 such that at least an interior of the calibration tool 150 and the microphone 115 are part of a closed (e.g., airtight) system. In some embodiments, the method can comprise emitting, by the calibration tool 150, a calibrating sound having predetermined sound characteristics. In some embodiments, the method can comprise receiving, using the microphone 115, one or more detected sound characteristics of the calibrating sound. In some embodiments, in an instance in which a comparison of the one or more detected sound characteristics of the calibrating sound received by the microphone 115 and the sound characteristics of the calibrating sound is indicative of a calibration error, calibrating the noise sensor relative to the calibrating sound. In some embodiments, calibrating the noise sensor relative to the calibrating sound can comprise calibrating the microphone 115. In some embodiments, calibrating the noise sensor relative to the calibrating sound can comprise calibrating the sensor PCB 114.

In some embodiments, by positioning the noise sensor between the speaker 111 and the wearer's ear, the noise sensor can be operable to capture noise having sound characteristics that closely approximates the sound characteristics of the noise to which the wearer is acoustically exposed while wearing the hearing protection device 10.

In some embodiments, it can be advantageous to form a securing structure or housing for holding a noise sensor in place within an ear cup of a hearing protection device, earmuffs, headphones, or the like. In some embodiments, the noise sensor can be coupled to a printed circuit board (PCB). In some embodiments, the noise sensor can be soldered to the PCB. In some embodiments, the noise sensor can be electrically coupled to the PCB. In some embodiments, the noise sensor can be held within a housing that is coupled to, formed from, or fixed to an inner volume of an ear cup of the hearing protection device. In some embodiments, the noise sensor can be at least partially enclosed within a housing. In some embodiments, the housing can be configured such that the noise sensor is partially or fully airtight. In some embodiments, the housing can be configured such that the noise sensor can be in acoustic communication with a speaker and/or the inner volume of an ear cup.

In some embodiments, the ear cup can be assembled, at least in part, by temporarily deforming the wider portion at or near the distal end of the housing and fitting the wider portion through the aperture from the inside of the external casing of the ear cup, soldering or otherwise electrically coupling the microphone to the PCB, and disposing the microphone through an opening at the proximal end of the housing until the microphone comes to rest on the ledge or slot defined at a transition point where the proximal portion of the axial bore narrows to define a proximal end of the distal portion of the axial bore. In some embodiments, the housing can be a monolithic structure in order to facilitate the airtight nature of the interior region of the ear cup during use of the hearing protection device and the airtight nature of the axial bore during calibration of the microphone.

In some embodiments, the housing 116 can be configured to have suitable mechanical properties such that the microphone 118 is securely retained within the housing 116, while the housing 116 provides some amount of attenuation of vibrations caused by movement of the hearing protection device 10 by the wearer, by sound waves from nearby sound sources such as speakers and/or the environment outside the ear cup 100, and the like. For example, the housing 116 may be made of rubber or a rubber-like material. Furthermore, in some embodiments in which the housing 116 is a monolithic structure formed as a single piece or component, some benefits of the invention include a reduction in number and complexity of components required for noise sensing in the hearing protection device leading to a reduction in manufacturing cost and complexity, a reduction in probability of component failure, and a reduced occupied volume leading to a smaller possible ear cup 100 profile. Also, since the microphone 118 can be calibrated, the accuracy of noise detection will be improved. Furthermore, since the microphone 118 can be calibrated without significant disassembly of the ear cup 100, the cost, time, and complexity of calibration of the microphone 118 are reduced. Furthermore, since the axial bore 123 of the housing 116 is dimensioned and configured to slidably and sealably receive the standard calibration tool 150 during calibration of the microphone 118, the in situ calibration of the microphone 118 is more effective, meaning the accuracy of the calibrated microphone 118 for this hearing protection device 10 is greater than microphones of conventional hearing protection devices that are not able to be calibrated at all, not able to be calibrated after assembly of the hearing protection device, and/or can only be calibrated in less than airtight environments.

In some embodiments, the exterior casing 117 of the ear cup 100 and the removable securing collar 111 can comprise or be formed from any suitably durable yet light material, such as a plastic material like acrylonitrile butadiene styrene (ABS) or the like. In some embodiments, the internal dust protector 119 can comprise or be formed from any suitable filtering material, such as Gore filtration material PE 120205 and other suitable ingress protection (IP) filter materials. In some embodiments, the internal dust protector 119 can be further configured to prevent flux of water between the distal portion of the axial bore 113 of the housing 116 and the noise sensor assembly disposed in the noise sensor receiving portion 125 proximate the distal portion of the axial bore 123 of the housing 116, thus preventing moisture damage to the sensor PCB 114a and/or the microphone 118. In some embodiments, the housing 116 can comprise or be formed from any suitably durable and yet deformable material, such as a synthetic rubber like ethylene propylene diene monomer (EPDM) rubber and the like. In some embodiments, the dust protector 123 can comprise or be formed from any suitable dust filtering material such as a foam, a mesh, a woven fiber, and the like.

In some embodiments, the ear cup 100 can further comprise an external microphone 140 configured as a noise sensor to sense noise exposure immediately outside the ear cup 100. For instance, the external microphone 140 can be configured to measure noise from outside the ear cup 100 to which the wearer would be exposed if the hearing protection device 10 was not used. As such, the hearing protection device 10 can be configured such that the speaker and noise sensor assembly 110, the external microphone 140, other suitable computing devices and/or circuitry, or other devices can be caused to transmit and/or store noise exposure data during use of the hearing protection device 10. In some embodiments, a signal indicative of a magnitude of noise exposure can be transmitted from the microphone 115 and/or the external microphone 140 to the main PCB or other suitable computing devices or circuitry, a memory device, or the like. In some embodiments, the magnitude of noise exposure measured by the microphone 115 can be compared to the magnitude of noise exposure measured by the external microphone 140 to determine the effectiveness of the active and/or passive noise dampening capabilities of the hearing protection device 10 and to identify when a noise sensor is in need of calibration or is malfunctioning.

In some embodiments, the microphone 115 can comprise a silicon wafer having a movable membrane and a fixed back plate over a cavity in the base wafer. In some embodiments, the sensor back plate can have a stiff perforated structure. In some embodiments, the microphone 115 can be a micro-electro-mechanical system (MEMS) microphone. Without wishing to be bound by any particular theory, in response to air movements related to noise exposure, the movable membrane of the microphone 115 can move, causing a change in a magnitude of a capacitance between the movable membrane and the fixed back plate, which can be converted by any suitable ASIC to an electrical signal. For instance, the ASIC can use a charge pump to place a fixed charge on the movable membrane of the microphone 115, and the ASIC can then measure voltage variations caused by capacitance changes related to movements of the movable membrane relative to the fixed back plate. While the microphone 115 can comprise the above-mentioned components according to some embodiments, the microphone 115 can comprise any suitable combination of components such that noise exposure can be sensed.

In some embodiments, the sensor PCB 114 and/or the flexible PCB 121 can comprise an insulated substrate supporting a plurality of electrical components and conductive tracks, and can be configured to communicate electrical signals and data between computing devices and other related circuitry. In some embodiments, the sensor PCB 114 can be configured to receive the electrical signal from the microphone 115, for example from the ASIC, the electrical signal indicative of the movement of the movable membrane of the microphone 115 in response to a magnitude of air movements related to a magnitude of noise exposure. While the sensor PCB 114 can comprise the above-mentioned components according to some embodiments, the sensor PCB 114 can comprise any suitable combination of components such that a signal received from the microphone 115 can be transmitted and/or interpreted relative to a magnitude of noise exposure sensed by the microphone 115.

In some embodiments, the speaker and noise sensor assembly 110 for the hearing protection device 10 can comprise a speaker 111 dimensioned and configured to be disposed within an ear cup 100 of the hearing protection device 10. In some embodiments, the speaker and noise sensor assembly 110 can further comprise a sensor housing 112 defining an axial bore 113 having a proximal end and a distal end, the sensor housing 112 disposed along a center axis of the speaker 1111. In other words, the sensor housing 112 and the sensor assembly 110 in general can be positioned immediately above and/or abutting the speaker 111 and/or the speaker housing 116. In some embodiments, the noise sensor can comprise a microphone 115 electrically coupled to the sensor PCB 114. In some embodiments, the noise sensor can be configured to receive acoustic signals via the axial bore 113 of the sensor housing 112 such that the noise sensor is in acoustic communication with the speaker 111 via the distal end of the axial bore 113. In some embodiments, the sensor housing 112 can comprise at least one of a vibration attenuation material and a noise dampening material. In some embodiments, the axial bore 113 of the sensor housing 112 comprises a first portion having a first inner diameter and a second portion distal the first portion having a second inner diameter less than the first inner diameter.

In some embodiments, the speaker and noise sensor assembly can be configured such that the sensor housing 112 is engaged with a side of the speaker housing 116 that is opposite the speaker 111. In some embodiments, the axial bore 113 is open on the distal end and the axial bore 113 is oriented away from the speaker 111. In some embodiments, the speaker housing 116 can at least partially define a cavity in which the noise sensor is disposed. In some embodiments, the opening at the distal end of the axial bore 113 is only open to the cavity defined at least partially by the speaker housing 116. In some embodiments, the speaker housing 116 can define a recess configured to receive a portion of the noise sensor therein. In some embodiments, the noise sensor is sealingly disposed against a surface of the sensor housing 112 such that the microphone 115 is positioned at the proximal end of the axial bore 113. In some embodiments, the axial bore 113 of the sensor housing 112 can be dimensioned and configured to slidably receive a calibration tool 150 to form an airtight seal with an inner surface of the sensor housing 112, such that the microphone 115 is configured to be disposed within a closed system during calibration. The closed system may be closed at the noise sensor end by the seal between the noise sensor and the sensor housing 112.

In some embodiments, the speaker and noise sensor assembly can further comprise a speaker housing 116 disposed proximate the speaker 111, wherein the sensor housing 112 is engaged with the speaker housing 116. In some embodiments, the sensor housing 112 can be configured to be securely disposed against a surface of the speaker housing 116. In some embodiments, the noise sensor can be configured to be disposed in a cavity defined at least partially between the sensor housing 112 and the speaker housing 116. In some embodiments, the sensor housing 112 can further define one or more securing apertures 112j, 112g extending through the sensor housing in a direction substantially parallel to the axial bore 113. In some embodiments, the one or more securing apertures 112j, 112g can be adapted to contact and secure the sensor housing 112 with respect to the speaker housing 116.

In some embodiments, the speaker and noise sensor assembly can further comprise an internal dust protector 123 disposed between the microphone 115 and the sensor housing 112, wherein the internal dust protector 123 is disposed between the microphone 115 and the sensor housing 112 to prevent contaminants from contacting the microphone 115. In some embodiments, the PCB is a microphone PCB and the speaker and noise sensor assembly can further comprise a flexible PCB operably coupled to the microphone PCB. As used herein, sensor PCB and microphone PCB are used interchangeably. In some embodiments, the speaker and noise sensor assembly can further comprise a main PCB operably coupled to the microphone PCB via the flexible PCB.

In some embodiments, the speaker and noise sensor can further comprise a securing member comprising one or more securing ridges, the securing member configured such that the sensor housing can be securely coupled to the securing member by slidably disposing the one or more securing ridges of the securing member into the one or more securing apertures of the sensor housing. For instance, in some embodiments, the securing member can be disposed on or defined by the speaker sensor 116.

In some embodiments, a hearing protection device 10 can comprise the speaker and noise sensor assembly 110 disposed within an ear cup 100, the ear cup 100 comprising an external casing, an inside surface, and a cushioning material disposed about the inside surface between the inside surface and the external casing. In some embodiments, the inside surface and/or the cushioning material can define or comprise the ear pad 120. In some embodiments, in an instance in which the cushioning material is sealably disposed against the user's head about the user's ear, an inner volume of the ear cup 100 is substantially airtight. In some embodiments, the hearing protection device 10 can comprise the speaker and noise sensor assembly 110 as described above, disposed within the ear cup 100, the hearing protection device 10 further comprising an external noise sensor assembly 140 comprising a second microphone acoustically coupled with an exterior of the hearing protection device 10, wherein the hearing protection device 10 is configured to compare signals from the noise sensor and the external noise sensor assembly.

As such, in some embodiments, a method of calibrating the noise sensor of the speaker and noise sensor assembly 110 described herein can comprise disposing a calibration tool 150 into the axial bore 113 of the sensor housing 112 via the distal end such that an interior of the calibration tool 150 and the microphone 115 are part of a closed system. In some embodiments, the method can further comprise emitting, by the calibration tool 150, a calibrating sound having predetermined sound characteristics and receiving, using the microphone 115, one or more detected sound characteristics of the calibrating sound. In some embodiments, the method can further comprise, in an instance in which a comparison of the one or more detected sound characteristics of the calibrating sound received by the microphone 115 and the sound characteristics of the calibrating sound is indicative of a calibration error, calibrating the noise sensor relative to the calibrating sound. In some embodiments, the method can further comprise disposing the calibration tool 150 into an axial bore of a sensor housing for an external noise sensor assembly 140 such that an interior of the calibration tool and an external microphone are part of the closed system, such that both the internal and external microphones may be calibrated simultaneously and may be calibrated relative to each other within the same closed system. For example, in operation, the signals received by the internal microphone and the external microphone may be compared with each other to determine the amount of cancellation needed and/or achieved by the hearing protection device. The internal microphone noise exposure level may indicate the amount of sound entering the user's ear, while the external microphone may indicate the total noise exposure at the exterior of the hearing protection device, and the difference between these values may inform many functions of the hearing protection device, such as the effect of the passive and/or active noise cancellation, identification of external sound versus sound originating from the speakers, and the like. Thus, the relative calibration of the two microphones may be as important as their absolute calibration, since the difference between the two noise exposure readings may be important. As such, the calibration tool may include tubes that extend into airtight communication with both the internal and external microphones of both ear cup assemblies to calibrate each of the four sensors within the same closed, airtight system. In some embodiments, the method can further comprise emitting, by the calibration tool 150, the calibrating sound having the predetermined sound characteristics and receiving, using the external microphone, the one or more detected sound characteristics of the calibrating sound. In some embodiments, the method can further comprise, in an instance in which a comparison of the one or more detected sound characteristics of the calibrating sound received by the external microphone and the sound characteristics of the calibrating sound is indicative of the calibration error, calibrating the external noise sensor relative to the calibrating sound.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The hardware used to implement the various illustrative logics, logical blocks, modules, and circuits described in connection with the aspects disclosed herein may include a general purpose processor, a digital signal processor (DSP), a special-purpose processor such as an application specific integrated circuit (ASIC) or a field programmable gate array (FPGA), a programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively or in addition, some steps or methods may be performed by circuitry that is specific to a given function.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the supply management system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

What is claimed is:

1. A speaker and noise sensor assembly for a hearing protection device, the speaker and noise sensor assembly comprising:
    a speaker dimensioned and configured to be disposed within an ear cup of the hearing protection device;
    a sensor housing defining an axial bore having a proximal end and a distal end, the sensor housing disposed along a center axis of the speaker;
    a noise sensor comprising a first microphone electrically coupled to a printed circuit board (PCB), the noise sensor configured to receive acoustic signals via the axial bore of the sensor housing such that the noise sensor is in acoustic communication with the speaker via the distal end of the axial bore; and
    an external noise sensor assembly comprising a second microphone acoustically coupled with an exterior of the hearing protection device,
    wherein the speaker and noise sensor assembly is configured to compare a magnitude of noise exposure measured by the first microphone and a magnitude of noise exposure measured by the second microphone to determine the effectiveness of the hearing protection device and to identify when the noise sensor is in need of calibration, and
    wherein the axial bore of the sensor housing is dimensioned and configured to slidably receive, via the distal end, a calibration tool to form an airtight seal with an inner surface of the sensor housing, such that the first microphone is configured to be disposed within a closed system during calibration.

2. The speaker and noise sensor assembly of claim 1, wherein the noise sensor is sealingly disposed against a surface of the sensor housing such that the first microphone is positioned at the proximal end of the axial bore in acoustic communication with the distal end of the axial bore.

3. The speaker and noise sensor assembly of claim 1, further comprising:
    a speaker housing disposed proximate the speaker, wherein the sensor housing is engaged with the speaker housing.

4. The speaker and noise sensor assembly of claim 3, wherein the sensor housing is engaged with a side of the speaker housing that is opposite the speaker.

5. The speaker and noise sensor assembly of claim 3, wherein the speaker housing at least partially defines a cavity in which the noise sensor is disposed.

6. The speaker and noise sensor assembly of claim 1, wherein the axial bore is open on the distal end and sealed at or proximate the proximal end by the noise sensor, and wherein the axial bore is oriented away from the speaker.

7. The speaker and noise sensor assembly of claim 6, wherein the sensor housing is configured to be securely disposed against a surface of the speaker housing, wherein the noise sensor is configured to be disposed in a cavity defined at least partially between the sensor housing and the speaker housing.

8. The speaker and noise sensor assembly of claim 6, wherein the sensor housing further defines one or more securing apertures extending through the sensor housing in a direction substantially parallel to the axial bore, wherein the one or more securing apertures are adapted to contact and secure the sensor housing with respect to the speaker housing.

9. The speaker and noise sensor assembly of claim 1, further comprising:
a securing member comprising one or more securing ridges, the securing member configured such that the sensor housing can be securely coupled to the securing member by slidably disposing the one or more securing ridges of the securing member into the one or more securing apertures of the sensor housing.

10. The speaker and noise sensor assembly of claim 1, wherein the axial bore of the sensor housing comprises a first portion having a first inner diameter and a second portion distal the first portion having a second inner diameter less than the first inner diameter.

11. A method of calibrating the noise sensor of the speaker and noise sensor assembly of claim 1, the method comprising:
disposing a calibration tool into the axial bore of the sensor housing via the distal end such that an interior of the calibration tool and the first microphone are part of a closed system that is substantially air tight;
emitting, by the calibration tool, a calibrating sound into the closed system having predetermined sound characteristics;
receiving, using the first microphone, one or more detected sound characteristics of the calibrating sound; and
in an instance in which a comparison of the one or more detected sound characteristics of the calibrating sound received by the first microphone and the sound characteristics of the calibrating sound is indicative of a calibration error, calibrating the noise sensor relative to the calibrating sound.

12. The method of claim 11, further comprising:
disposing the calibration tool into an axial bore of an external sensor housing such that an interior of the calibration tool and the second microphone are part of the closed system;
emitting, by the calibration tool, the calibrating sound having the predetermined sound characteristics;
receiving, using the second microphone, the one or more detected sound characteristics of the calibrating sound; and
in an instance in which a comparison of the one or more detected sound characteristics of the calibrating sound received by the second microphone and the sound characteristics of the calibrating sound is indicative of the calibration error, calibrating the external noise sensor relative to the calibrating sound.

13. A hearing protection device comprising:
an ear cup comprising an external casing, an inside surface, and a cushioning material disposed about the inside surface between the inside surface and the external casing, wherein, in an instance in which the cushioning material is sealably disposed against a user's head about the user's ear, an inner volume of the ear cup is substantially airtight;
a speaker dimensioned and configured to be disposed within the ear cup;
a sensor housing defining an axial bore having a proximal end and a distal end, the sensor housing disposed along a center axis of the speaker;
a noise sensor comprising a first microphone electrically coupled to a printed circuit board (PCB), the noise sensor configured to receive acoustic signals via the axial bore of the sensor housing such that the noise sensor is in acoustic communication with the speaker via the distal end of the axial bore; and
an external noise sensor assembly comprising a second microphone acoustically coupled with an exterior of the hearing protection device,
wherein the speaker and noise sensor assembly is configured to compare a magnitude of noise exposure measured by the first microphone and a magnitude of noise exposure measured by the second microphone to determine the effectiveness of the hearing protection device and to identify when the noise sensor is in need of calibration, and
wherein the axial bore of the sensor housing is dimensioned and configured to slidably receive, via the distal end, a calibration tool to form an airtight seal with an inner surface of the sensor housing, such that the first microphone is configured to be disposed within a closed system during calibration.

14. The hearing protection device of claim 13, wherein the noise sensor is sealingly disposed against a surface of the sensor housing such that the first microphone is positioned at the proximal end of the axial bore in acoustic communication with the distal end of the axial bore.

15. The hearing protection device of claim 13, further comprising:
a speaker housing disposed proximate the speaker, wherein the sensor housing is engaged with a side of the speaker housing that is opposite the speaker.

16. The hearing protection device of claim 15, wherein the speaker housing at least partially defines a cavity in which the noise sensor is disposed.

17. The hearing protection device of claim 13, wherein the axial bore is open on the distal end and sealed at or proximate the proximal end by the noise sensor, and wherein the axial bore is oriented away from the speaker.

18. The hearing protection device of claim 17, wherein the sensor housing is configured to be securely disposed against a surface of the speaker housing, wherein the noise sensor is configured to be disposed in a cavity defined at least partially between the sensor housing and the speaker housing.

19. The hearing protection device of claim 17, wherein the sensor housing further defines one or more securing apertures extending through the sensor housing in a direction substantially parallel to the axial bore, wherein the one or more securing apertures are adapted to contact and secure the sensor housing with respect to the speaker housing.

20. The hearing protection device of claim 13, further comprising:
   a securing member comprising one or more securing ridges, the securing member configured such that the sensor housing can be securely coupled to the securing member by slidably disposing the one or more securing ridges of the securing member into the one or more securing apertures of the sensor housing.

* * * * *